(12) United States Patent
Watson et al.

(10) Patent No.: US 6,778,271 B2
(45) Date of Patent: Aug. 17, 2004

(54) MEASUREMENT OF PARTICLE SIZE DISTRIBUTION

(75) Inventors: David John Watson, Hanley Swan (GB); Clive Patrick Ashley Catterall, Malvern Wells (GB); Duncan Edward Stephenson, Worcester (GB)

(73) Assignee: Malvern Instruments Limited (GB)

( * ) Notice: Subject to any disclaimer, the term of this patent is extended or adjusted under 35 U.S.C. 154(b) by 0 days.

(21) Appl. No.: 09/378,666

(22) Filed: Aug. 20, 1999

(65) Prior Publication Data

US 2003/0030802 A1 Feb. 13, 2003

(30) Foreign Application Priority Data

Aug. 22, 1998 (GB) .............................. 9818348

(51) Int. Cl.[7] .............................................. G01N 15/02
(52) U.S. Cl. .................... 356/336; 356/337; 356/341; 356/342; 356/343
(58) Field of Search ................... 356/335–343; 250/574, 575; 257/57, 59, 66, 347, 349, 352, 353, 72

(56) References Cited

U.S. PATENT DOCUMENTS

| | | | | | |
|---|---|---|---|---|---|
| 3,901,602 A | * | 8/1975 | Gravatt, Jr. | ................. | 356/336 |
| 4,361,403 A | | 11/1982 | Loos | | |
| 4,541,719 A | | 9/1985 | Wyatt | | |
| 4,595,291 A | * | 6/1986 | Tatsuno | ..................... | 356/336 |
| 4,801,205 A | * | 1/1989 | Tatsuno | ..................... | 356/336 |
| 4,953,978 A | * | 9/1990 | Bott et al. | .................. | 356/336 |
| 5,012,119 A | * | 4/1991 | Rhiner | ....................... | 356/343 |
| 5,185,641 A | * | 2/1993 | Igushi et al. | ................ | 356/336 |
| 5,416,580 A | * | 5/1995 | Trainer | ...................... | 356/336 |
| 5,428,443 A | * | 6/1995 | Kitamura et al. | ........... | 356/338 |
| 5,576,827 A | | 11/1996 | Strickland | | |
| 5,796,480 A | * | 8/1998 | Igushi | ....................... | 356/336 |

FOREIGN PATENT DOCUMENTS

| | | | |
|---|---|---|---|
| EP | 0485817 A1 | | 5/1992 |
| EP | 0559529 A1 | | 9/1993 |
| GB | 1304962 | | 1/1973 |
| JP | 05034259 | * | 2/1993 |
| JP | 08178830 | * | 7/1996 |

* cited by examiner

Primary Examiner—Frank G. Font
Assistant Examiner—Sang Hoang Nguyen
(74) Attorney, Agent, or Firm—John P. White; Cooper & Dunham LLP

(57) ABSTRACT

A particle size distribution analysis apparatus comprising a sample measurement zone adapted to define a sample of particles, a light emitting means adapted to provide a source of light incident upon the sample measurement zone, and at least a first detection means adapted to measure light levels in the apparatus at particular scattering angles and output a signal to a computation means enabling the particle size distribution of particles contained within the sample to be determined, wherein the computation means is adapted, in use, to calculate a particle size distribution taking into account reflections by the measurement zone of light scattered off the particles.

22 Claims, 5 Drawing Sheets

MEASUREMENT OF PARTICLE SIZE DISTRIBUTION

BACKGROUND OF THE INVENTION

1. Field of the Invention

This invention relates to an improved apparatus and method for measuring particle size distribution.

2. Description of Related Art

It is known to provide particle apparatus which have a light emitting means to irradiate a sample of particles with light and to provide detection means to measure the light reflected and/or diffracted by the particles in order to determine the particle size distribution of the particles. Such known systems provide a plurality of detectors, generally in a plane, around a sample measurement zone. Such a system is shown in WO 90/10215 wherein an arc of detectors is provided substantially perpendicular to a beam of light incident upon the sample of particles.

It will be appreciated that the term particle may mean any phase of a discontinuous material contained within a continuous phase of a supporting medium. Either phase may be gaseous, liquid or solid. The only physical limitation is that the particle must have a different refractive index to the medium and further, that the medium must be substantially transparent at any illuminating wavelength of light.

SUMMARY OF THE INVENTION

According to a first aspect of the invention there is provided a particle size distribution analysis apparatus comprising a sample measurement zone adapted to define a sample of particles, a light emitting means adapted to provide a source of light incident upon the sample measurement zone, and at least a first detection means adapted to measure light levels in the apparatus at particular scattering angles and output a signal to a computation means enabling the particle size distribution of particles contained within the sample to be determined, wherein the computation means is adapted, in use, to calculate a particle size distribution taking into account reflections of light scattered off the particles by the measurement zone.

An advantage of such an approach is that the apparatus is more accurate than prior art apparatus. Previously particle size distribution analysis apparatus has measured the scattering of light from particles to perform the size distribution calculations. Reflection of the scattered light have led to inaccuracies in the calculations which were previously thought to be immaterial. It has been realised that the inaccuracies are in fact material and should be allowed for.

Preferably a second detection means is provided and the computation means is adapted, in use, to modify the readings taken from the first detection means based upon the readings taken from the second detection means to take in to account reflections.

Providing a second detection means and using readings taken from the second detection means to modify the readings taken from the first is beneficial in that the computational load on the computational means is reduced. Possibly the computational load is reduced by a factor of two.

Preferably the computation means is adapted, in use, to modify the readings taken from the second detection means based upon the readings taken from the first detection means to take in to account reflections. This may also reduce the computational load and improve the accuracy of the system.

The measurement zone may comprise at least a pair of spaced windows adapted to contain the sample. The windows may be glass, plastics, or some other material transparent to the light emitted by the light emitting means. The windows may be substantially parallel to one another.

Such windows have been used in prior art apparatus and are known. However, the materials used for the windows reflect light incident upon them. Such reflections are unwanted and can be detected by the detection means which interprets the reflections as scattering from the particles in the sample which lead to inaccuracies in the particle size distributions calculated by the computation means. The present apparatus may be adapted to modify the readings taken from the first detection means with readings taken by the second detection means in order to account for the reflections from the windows.

The windows may be coated in an anti-reflective coating which is adapted, in use, to reduce unwanted reflections.

The first detection means may comprise a large angle detector which may be situated substantially at a large angle from the axis of the beam of light emitted from the light emitting means taking the direction of travel of the light as 0°. A large angle may be substantially in the range 90° to 40° may be substantially 70° to 40°.

The second detection means may comprise a back scatter detector which may be situated substantially at an obtuse angle from the axis of the beam of light emitted from the light emitting means taking the direction of travel of the light as 0°. The obtuse angle may be substantially in the range 90° to 180°, may be in the range of about 110° to about 170°.

There may be provided a plurality of back scatter detectors (second detection means). In the preferred embodiment there may be provided two back scatter detectors. In one embodiment the second detection means may comprise a detector placed at substantially 120° and may comprise a further detector placed at substantially 135°.

There may be provided a plurality of large angle detectors (first detection means) and in the preferred embodiment there may be provided two large angle detectors. In one embodiment the first detection means may comprise a detector placed at substantially 45° and may comprise a further detector placed at substantially 60°.

Preferably there are the same number of first and second detection means.

The light emitting means may be a laser which emits a beam of light.

Preferably the angle at which the first detection means and the second detection means are inclined symmetrically relative to the measurement zone. That is if the first detection means in inclined at an angle θ relative to a beam of light emitted from the light emitting means the second detection means may be inclined at 180° −θ. Indeed, if there are a plurality of first detection means and the same number of second detection means each of the first and second detection means may be inclined symmetrically to the measurement zone. Such an arrangement is advantageous in that it simplifies subsequent calculations to allow for the multiple reflections.

Preferably the first and second detectors are of substantially the same construction. This is convenient and makes the calculation of the multiple reflections easier; allowance does not have to be made for differences in the detectors.

According to a second aspect of the invention there is provided a method of improving the accuracy of a particle size distribution calculation performed by illuminating a sample with light from a light emitting means and taking readings of the amount of light scattered by the sample comprising providing at least a first detection means and calculating a particle size distribution taking into account reflections of light scattered from the particles by the measurement zone.

An advantage of such a method is that it can lead to more accurate results than prior methods. The method may be thought of as adjusting the data provided by the detection means to take account of known reflection terms. The modification of the readings may be used to allow for unwanted reflections within the apparatus which could lead to inaccurate results.

Preferably a second detection means is provided and the readings taken from the first detection means are modified by readings taken from the second detection means. This is advantageous in that the computational load is reduced.

Preferably the reading taken from the second detection means is modified by readings taken by the first detection means. Again, this may improve the accuracy of the system.

Preferably the method comprises compensating a reading from a detection means detecting light scattered having a directional component toward the light emitting means with a readings from a detection means detecting scattered light having no directional component toward the light emitting means. This may be thought of as compensating readings taken for back scattered light with readings taken for forward scattered light.

The method may also comprise compensating a reading from a detection means detecting light having no directional component toward the light emitting means with a reading from a detection means detecting scattered light having a directional component toward the light emitting means. This may be thought of as compensating readings taken for forward scattered light with readings taken for back scattered light.

Preferably the two detection means are provided at substantially symmetric angles relative to the measurement zone. This has the advantage that the calculations necessary to modify the readings are simplified.

The first detection means may comprise a plurality of detectors. Likewise the second detection means may comprise a plurality of detectors. The method may comprise integrating the signals received by the first detection means to obtain a reading and further comprise integrating the signal received by the second detection means to obtain a reading.

The method may be thought of as reducing the likelihood of the occurrence of inaccurate particle size distribution predictions. The unwanted reflections within the apparatus may lead to the detection means detecting particle sizes which are not actually present in the sample.

BRIEF DESCRIPTION OF THE DRAWINGS

There now follows by way of example only a detailed description of an embodiment of the invention with reference to the accompanying drawings of which.

DETAILED DESCRIPTION OF PREFERRED EMBODIMENTS

Figure 2:
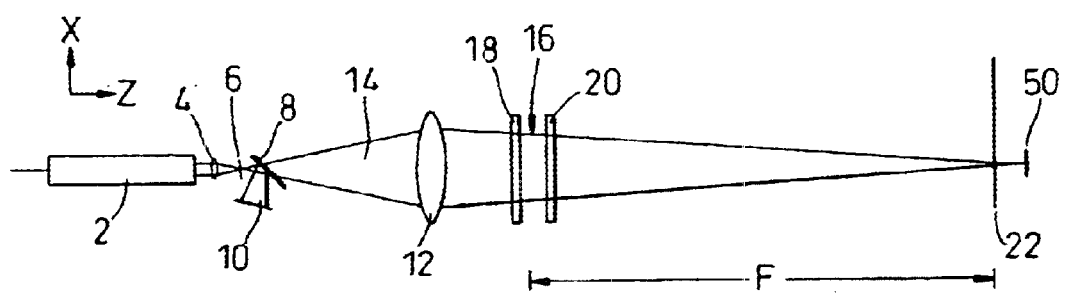
FIG. 2 shows a basic system configuration.

FIG. 2 shows a schematic of a basic particle size distribution measuring apparatus wherein a low power laser source 2 (light emitting means), typically a He—Ne laser is beam expanded and spatially filtered to produce a larger collimated beam containing only the TEM 00 mode of laser propagation. A lens 4 and a spatial filter component 6 positioned in the focal plane of the lens 4 achieves this.

A beam splitter 8 is typically used in order to allow a small fraction of the laser power to be directed onto a laser monitor detector 10. This detector 10 allows the incident laser power to be monitored and any fluctuations corrected. It is important in the sub-micron measurement of particles to ensure that the laser power does not fluctuate between the sample and background measurement stages. For this reason optical sources are always either directly stabilised or monitored so that compensation can be performed. Non laser and semiconductor laser optical sources can be readily power controlled, however gas lasers need to operate in a steady state mode.

Although intensity control of a gas laser can be achieved by feeding the detector signal into the measurement electronics as gain compensation (for example it can be used to modulate the ADC reference voltage so that the ADC conversion characteristic is constant regardless of laser power) it is preferred to use a different and better approach. The laser power is read as a data value and allowed for by performing a scale correction during subsequent data processing by a signal processing unit.

A moveable shutter (not shown) which can be introduced under system control is provided to allow the laser illumination to be blocked from impinging on a sample cell without in fact removing power from the laser. This is a commonly employed approach for gas lasers, which do not respond well if turned off and on frequently. The purpose of the shutter is to allow the laser power to be removed in certain measurements of the detection system, for example, dark current and electronic offsets (and when using a second light source to scatter from the sample).

A range lens 12 then focuses the beam 14 so that a diffraction limited spot is produced in a plane of a focal plane detector 22. The laser beam also passes through a sample region 16 (or measurement zone) into which sample particles will be introduced.

In principle the sample region needs no physical parts to define it, since particles may be driven through the beam without any form of containment. However, it is preferred to provide a "sample cell" (acting as a sample containment means) in order to provide protection of the optical system and containment of any particle carrier fluids. A sample cell would typically consist of two glass windows 18, 20 spaced apart by a well defined distance which are built into a cell body (not shown) designed to contain and suspend/circulate the particles in a carrier medium.

The windows 18, 20 allow the access and egress of the laser beam and of scattered light from the sample particles over the required practical range of the system. The carrier medium may be liquid or gas, the most common media being water and air. The sample region or cell 16 is the intersection of the laser beam diameter with the space between the containment windows 18, 20.

The sample region 16 is positioned at a known distance F from the focus point of the laser beam. The dimension F is critical in that it defines, for a given set of components, the available size range of the system for the system shown in FIG. 2. If further detectors are added the particle size distribution which can be measured is extended.

Figure 6:
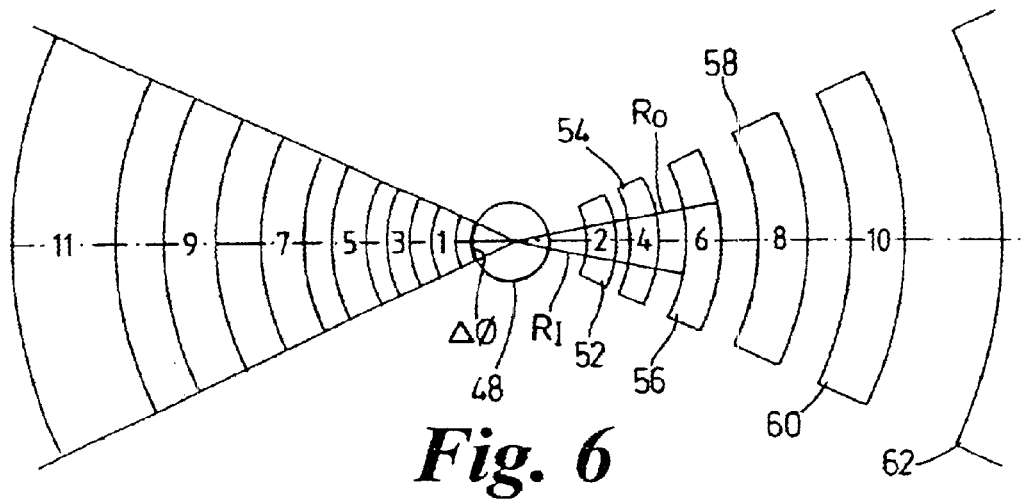
FIG. 6 shows an arrangement of detectors.

At the focal point of the laser beam a multi-element focal plane detector 22 is positioned, conventionally constructed as a single silicon photodiode array and an example of such a multi-element detector layout is shown in FIG. 6.

Figure 1:
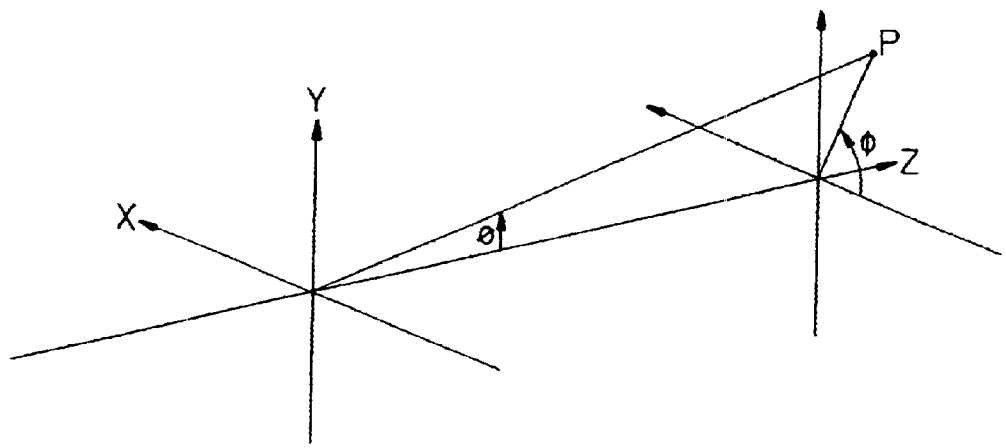
FIG. 1 shows the co-ordinate system used.

In the remaining description the following co-ordinate system has been used and is shown in FIG. 1. The direction of laser light propagation is assumed to be the positive Z direction. The X-Z plane is assumed to be the "horizontal plane" and Y-Z the "vertical" plane. The arrows indicate the positive direction for all co-ordinates. Angle θ indicates the scattering angle away from the laser axis Z to an arbitrary point P, in the plane containing both Z and P. The angle φ is the azimuthal angle from the X-Z plane around the Z axis to the point P.

Figure 3:
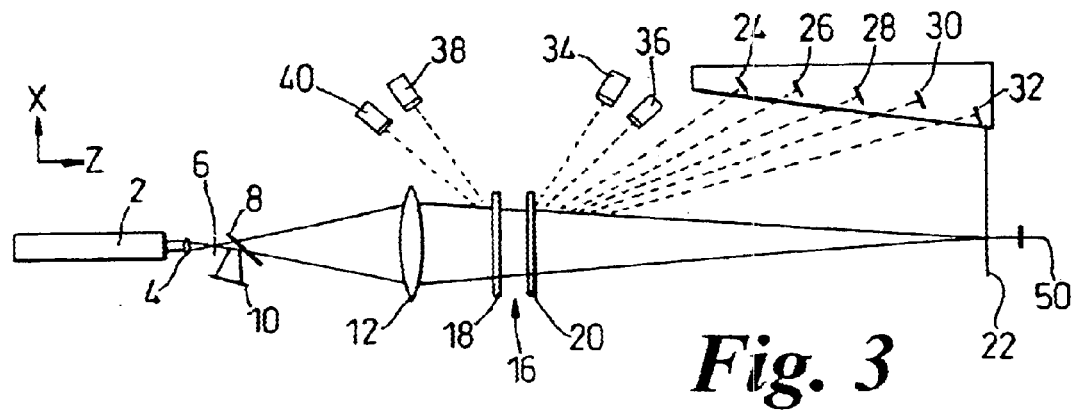
FIG. 3 shows an enhanced system configuration.
Figure 4:
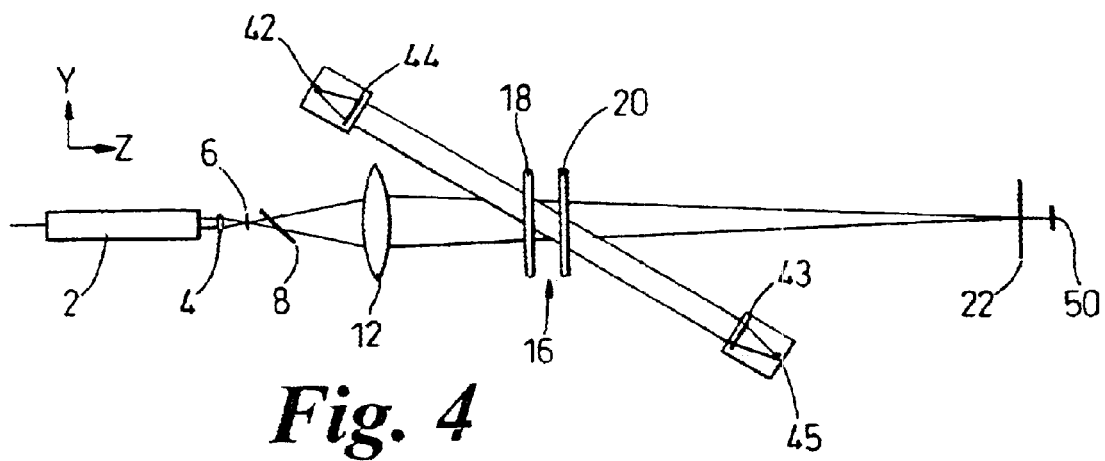
FIG. 4 shows a further enhancement of the system shown in FIG. 3.
Figure 5:
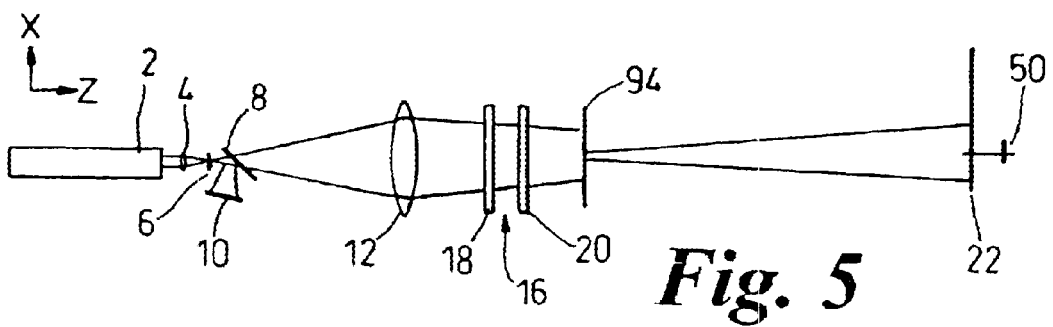
FIG. 5 shows an optical arrangement allowing the system to be calibrated.

Performance enhancing improvements to the basic system of FIG. 2, allowing smaller particles to be detected, are shown in FIGS. 3 and 4. The skilled person will realise that in some prior art systems multiple laser sources at different cell entry angles are used allowing the detector to be transformed into apparently new collection angles. Also, some prior art systems utilise multiple detection systems with a single laser source to achieve the same effect. Although not commonly employed any permutation of these principles is also possible.

In the preferred embodiment a further array of detectors is used to extend the optics described earlier as shown diagrammatically in FIG. 3. The extra detectors decrease the minimum size of particle which can be measured pushing the detectable particle size down to approximately 0.2 μm.

A series of nine forward angle detectors are provided although only five are shown in the FIGS. 24, 26, 28, 30, 32 on a PCB that rims the length of a cell-detector void. The detectors 24, 26, 28, 30, 32 are mounted physically aligned to face the cell 16. Each detector 24, 26, 28, 30, 32 is located at a special distance and angle from the cell 16 which is selected to optimise the information content of the entire system.

As the position of a detector departs from the focal plane of the lens 12 the detector no longer perfectly integrates over θ. Instead the detector measures signals over an additional Δθ which increases the nearer the detector is to the cell 16. This error in the angular collection of the detector can be predicted and therefore taken account of in a theoretical model of the system. In addition it is known that the light scattering characteristic changes more slowly as the angles become larger and thus the effect of the slight integration error becomes smaller and eventually negligible. The detectors 24, 26, 28, 30, 32 are provided and can be considered to be a simple angular continuation of the signal received on the focal plane detector 22. Indeed in the preferred embodiment the detectors 24, 26, 28, 30, 32 are routed into the same signal conversion electronics as the signals from the focal plane detector 22.

Because of the reducing angular dependence of the signal it is normal for the detectors 24, 26, 28, 30, 32 not to form a continuous angular sequence since no information can get "lost" in the gaps. Further, the detectors 24, 26, 28, 30, 32 are rectangular or circular standard components and not the angular ring structure of the focal plane detector 22.

At angles approaching 45° or greater a new problem in signal detection becomes relevant. The detectors 24, 26, 28, 30, 32 are operating as simple line of sight detectors and thus they see also the stray reflections from the cell 16 (and multiple reflections). At forward angles the scattering from particles is strongly dominant and the stray multiple reflections are safely ignored. At the larger angles the tilt of the cell brings the cell walls more directly into view and the particle scattering intensity is typically masked. That is the detector field of view eventually brings the cell wall into view and the detector consequently collects light reflected from the cell wall as well as light scattered by the particles. This forces consideration of the proper spatial filtering of the received detector signals at larger angles.

As a consequence for these larger angles (that is angle approaching 45° or greater) a detector is produced as a small element positioned in the focal plane of a collection lens. The combination forms a spatial filter, and ensures that the detector receives light only from a narrow collection angle. This allows the cell wall signals to be acceptably rejected and not interfere with the measurement. Because of this additional complexity these detectors are used sparingly and referred to as large angle detectors 34, 36 in FIG. 3.

A further enhancement of the basic system of FIG. 2 is also shown in FIG. 3 and comprises providing back scattering detectors 38, 40. These detect light scattered by particles from the rear of the cell; that is where 90°<θ<180°. This detection is particularly important for the sub-micron determination of particle size. However light scattered at backward angles has poor angular variation and thus there is little need to sample at small angular increments. The back scatter detectors 38, 40 have mirror symmetry with the large angle detectors 34, 36 about an X-Y plane passing through the sample cell, and are constructed in an identical manner. The mirror symmetry is a convenience that allows for a simple correction of the large angle 34, 36 and back scatter 38, 40 detectors for the high cell reflectivity that occurs at these large exit angles from the cell 16.

Thus the basic approach of the preferred embodiment has a detection means comprising a focal plane detector 22 of thirty three elements, a transmission detector 50, a forward angle array of nine further elements, two large angle detectors 34, 36 and two back scatter 38, 40 detectors. The detectors are all disposed in a single plane with respect to the laser polarisation plane.

FIG. 4 shows a schematic of a further enhancement of the system shown and described in relation to FIG. 2 which allows the system to measure particles to a size of less than 0.1 μm and to improve the resolution for particle sizes of less than 1 μm.

A second light source with a shorter wavelength than the laser 2 is provided and the large angle and back-scatter responses to this light are measured to gain the extra resolution. The use of shorter wavelengths is the key to the bottom end size reduction and the combination of the two wavelengths increases the available sub-micron resolution of the system.

The shorter the wavelength the greater the enhancement to the sub-micron range and resolution. However there are practical considerations that prevent a substantial reduction in wavelength at effective cost. Thus only visible light wavelengths may be a practical option. In the system of FIG.

4 an LED 42 (a light emitting means) which emits blue light has been used. Other sources such as a laser diode may be used.

The sub-micron performance is only enhanced by the large angle scattering from the additional optical measurement and small angle scattering is largely redundant as it is duplicating data in the original measurement. Thus there is no need to produce a reduced wavelength light source 42 capable of the same stringent spatial filtering as the main optical system. This means that the requirements for collimation of the second beam are reduced significantly since only large angle scattering needs to be measured and the light output of an LED or laser diode is sufficiently collimated and monochromatic.

Further, the source 42 need only be near monochromatic rather than have the wavelength purity of the laser source 2. This is because small wavelength errors are equivalent to small angular errors. For the large angles of interest the angular dependence of particle scattering is reduced and thus the wavelength spreading effect becomes negligible.

Thus the blue LED 42 or laser diode emitting a blue beam of light are two examples of suitable sources provided they have a narrow spectrum of output light, typically ±50 nm. The ability to use an LED or laser diode as the source significantly reduces the cost of implementation and improves the long-term robustness.

The shorter wavelength second light source 42 is provided off-axis to the laser source 2 and in a plane perpendicular to the plane formed by the detectors 24, 26, 28, 30, 32 and the large angle 34, 36 and the back scatter 38, 40 detectors. (That is FIG. 4 has been rotated 90° about the z axis relative to FIG. 3). If the angle of the beam from the second light source relative to the z axis is kept small it is possible to re-use the large angle 34, 36 and the back scatter 38, 40 detectors in measurements using both light emitted from the second light source 42 and the laser 2. This has the benefit of avoiding the cost of further detectors specifically for measurement of signals produced by the second light source 42. Although feasible it may not be considered necessary to utilise the larger angle elements of the detectors 24, 26, 28, 30, 32 for the short wavelength requirements (or we may re-use them in this way in other embodiments).

In the preferred embodiment the second light source 42 is provided at a shallow angle, typically 10–15° to the main beam path, sufficient to allow the optical components to co-reside without mechanical interference.

In one embodiment the second light source is an LED and has a wavelength of typically 466 nm and with a narrow spectral range, typically +/−30 nm half width, half height. The light emitted from the LED 42 is collected and collimated by a single lens 44 which projects a beam through the cell windows 18, 20 at the same physical location as the beam from the laser 2. Thus the same cell 18, 20 windows are effective for measurements from both the LED 42 and the laser 2 and there is no need for a dual cell configuration.

The LED 42 projects the blue beam through the cell 16 so that it superposes the area where the beam from the laser 2 intercepts in the cell 16 (preferably exactly superposes). The unscattered beam from the LED 42 exits the cell 16 and is collected by an LED transmission detector 45 that measures the transmission of the blue beam through the cell. This LED transmission detector 45 also requires spatial filtering in order to improve the angular resolution of the measurement. This is achieved by use of a detection scheme (identical to that of the large angle 34, 36 and back scatter 38, 40 detectors described earlier), having a small detector element 45 in the focal plane of a collection lens 43.

The structure of the focal plane detector 22 is shown in FIG. 6. A centre of the focal plane detector 22 comprises a structure that is designed to allow the monitoring of the unscattered laser beam power. This may be implemented in one of three forms, a hole drilled through the wafer from which the detector is fabricated, a detector structure built on the wafer surface, or a mirror-like element that reflects the laser beam off the surface to an auxiliary detector mounted elsewhere. Each solution is aimed at allowing a measure of the power of the focused spot, which gives the power of the unscattered laser 2 output power.

In the preferred embodiment the wafer 46 from which the focal plane detector 22 is fabricated is drilled completely through from front to back with a small hole 48 of exact diameter and positioning. The focal plane detector 22 is aligned with the laser beam so that the diffraction limited spot falls down through the hole and out of the rear of the focal plane detector 22. A P.C.B (not shown) supporting the wafer 46 is provided with suitable clearance holes to allow the beam to expand from the rear of the focal plane detector 22 and to fall onto a transmission detector 50.

In addition to the central hole 48 the focal plane detector comprises a series of annular ring detectors (51 to 62). Each detector is defined by an inner $R_i$ and an outer $R_o$ radial boundary, and an azimuthal angle $\Delta\phi$. The detectors may be constructed with a wide variation in the number of ring detectors provided and spacing in the spacing of each of the detectors, each different design trying to optimise the system. [For clarity, only twelve ring detectors are shown in FIG. 6, but there may be any other number. In one embodiment there are thirty-three detectors.]

If the focal plane detector 22 has no hole and the transmission detector were provided on the surface of the focal plane detector 22 then it is possible to construct the transmission detector 50 as three or four sub elements. The laser beam is then adjusted until it equalises the signal contribution from each sub-element, the sum of all element being used as the readings. Whilst this is a convenient layout it suffers from specific disadvantages. The first is that it depends on the beam having circular symmetry, whereas the real beam may have aberration. The second is that the detector structures are very small and are thus subject to significant error in dimensions through photolithography limitations.

In another embodiment the focal plane detector 22 has a hole at a centre portion and an auxiliary transmission detector 50 to measure the initial laser beam intensity and it is possible to similarly split this detector into sub elements. Again the beam is adjusted to balance the relative powers on the sub-elements with the entire signal being used as the transmission measure or level of initial laser beam power. This approach eliminates the problem of having detector elements of small sizes since the beam has expanded considerably by the time it hits a transmission detector 50 beyond the focal plane detector 22 and typically expands to substantially 3 mm. Thus, the sub-detectors of the transmission detector 50 can be larger with the same discrimination.

However it adds new difficulties in that the transmission detector 50 is normally mounted to the focal plane detector 22 by hand and thus its alignment with the centre of the focal plane detector 22 has to be calibrated during assembly in some way. Given the extreme precision involved this requires extra expense. In addition since in some systems multiple ranges are achieved by changing the distance F, the alignment of the detector normal to the Z direction must be exact to avoid the alignment point apparently moving at different range positions.

A single detector element provides an integration (over time) of the light scattered by particles into those angles received between the $R_i$ and $R_o$ boundaries. These angles are also determined by the cell 16—focal plane detector 22 distance F (as shown in FIG. 2). It may be possible to arrange the lens 12 so that cell 16 to focal plane detector 22 length F is varied. Such a variable arrangement allows a wider range of angles to be covered by the instrument in a series of size ranges determined by the distance F. In the preferred embodiment a single range lens 12 and a fixed cell 16—focal plane detector 22 distance, F, with range extension being achieved by the use of the large angle 34, 36, the back scatter 38, 40 and detectors 24, 26, 28, 30, 32.

In order to measure the largest possible particle sizes the inner detector 51 wants to measure the smallest angles possible and in practise means that the size of the central hole 48 needs to as small as is practical whilst collecting all of the beam from the laser 2 with the first detector as close to the boundary of the hole 48 as possible. The practical limits of photolithography and micromachining determine this smallest detector dimension.

In order to measure the smallest particle sizes the detectors need to subtend larger angles, eventually even back-scatter angles are required. There is a clear practical limit to the range of angles that can be covered by a system having only a focal plane detector 22. The limit is determined by the largest physical dimensions that can be integrated into the planar focal plane detector array and such systems are typically limited to angles up to 30°, which prevents accurate sizing below 0.3 µm.

Figure 7:
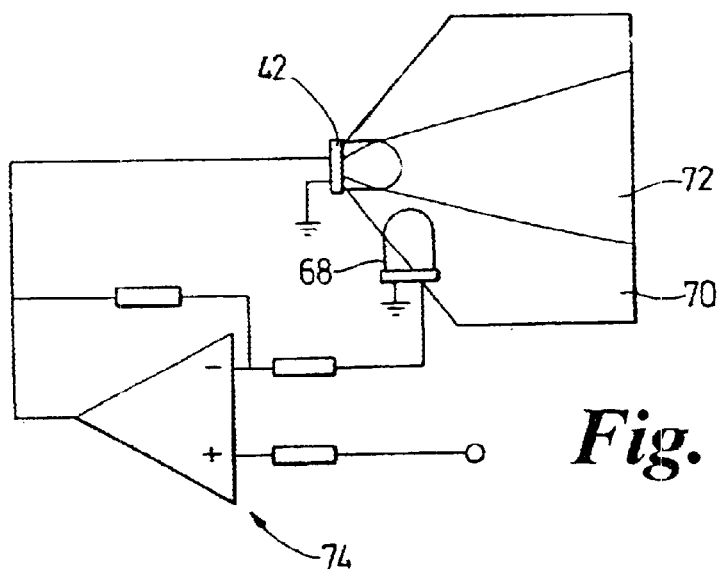
FIG. 7 shows a schematic circuit for stabilising a light source of FIG. 4.

As discussed hereinbefore the light sources must be stabilised or corrections made for the power fluctuation. Unlike the laser 2 the LED 42 has desirable properties with regard to light power control in that it can be turned on and off at will and rapidly stabilises in output power. It can also be readily temperature stabilised, and outputs relatively little heat. The output power can therefore be controlled by modulation of the LED 42 current. For these reasons the power control of the LED is accomplished by a closed loop electronic control system shown in FIG. 7.

The LED 42 output power is monitored by a stabilisation means which comprises a photodiode monitor 68 (primary monitoring means). The monitor 68 requires no beam splitter or special optics since the LED 42 has sufficient optical losses that the detector can monitor using the stray light 70 lost from the LED plastic body. The stray light is represented in the Figure by the outer region around the main beam 72 from the LED 42. The monitor 68 provides a feedback signal to a current control circuit 74 (or primary processing means) that varies current to the LED 42 until an output power is achieved that matches an input control demand.

In order to provide temperature compensation for the LED stabilisation means a further identical detector held in blackout conditions but under the same temperature environment may be used to provide a temperature stabilisation means. This allows the monitor signal to be compared differentially with the signal from the blacked out detector giving common mode rejection of temperature variation.

This provides a stable known output light intensity from the LED 42 that is entirely electronically servo controlled. This implies that the LED 42 power monitor does not require that it be fed into the computing element (as is done with the reading from the laser monitor detector 10), since it can be taken as pre-calibrated.

An alternative/different approach to providing the same control effect would be to feed the signal from the monitor 68 into the computational element 77 so that the gain compensation could be performed by digitally re-scaling the data obtained using the LED 42. (That is as is done with the signal from the laser monitor detector 10). This would avoid the need for closed loop control of the LED 42 power supply, which could instead then work as a constant current source. We prefer to stabilise the LED since it is an elegant solution and avoids unnecessarily complicated computational calculations.

In order to enter the data into a computational element 77 it is fundamentally necessary to multiplex parallel data produced by the system to a serial stream that can be read through a common interface. There are many conventional ways to perform this using electronic systems, analogue, digital or bus based multiplexers are all commonly utilised singly or mixed.

Figure 8:
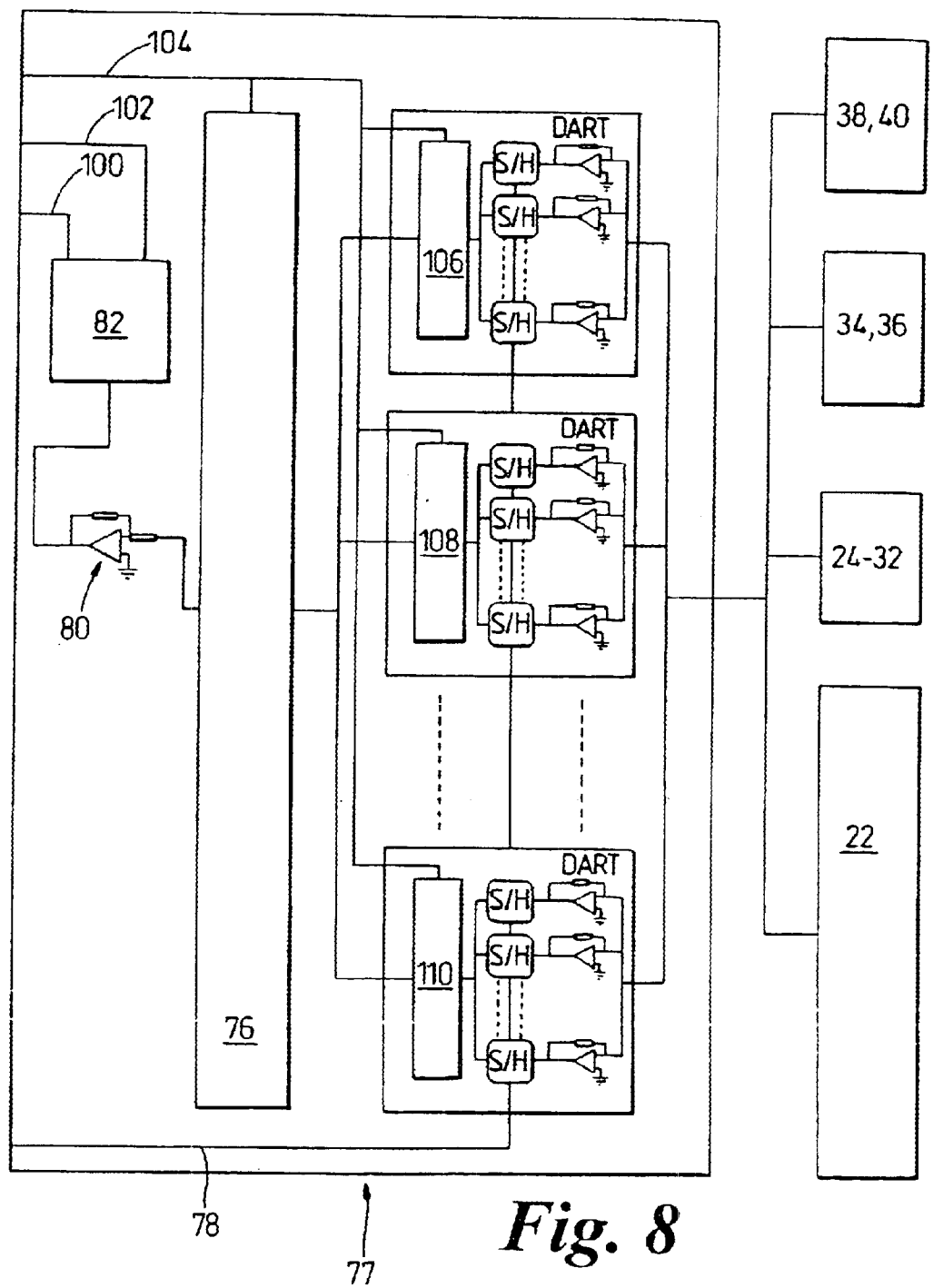
FIG. 8 shows a schematic of the signal and collection circuits of the system.

In the preferred embodiment the arrangement in FIG. 8 is used to process the data produced by the system. Each detector in the system (the detectors are represented on the right hand side of the Figure and are connected via busses to the remaining circuitry of the Figure), is provided with its own dedicated transimpedance gain amplifier followed by a sample and hold stage (represented by S/H in the Figure). The gain stage of the amplifier lifts the signal levels to a sufficient level to allow the following signal processing to introduce negligible error.

The sample and hold circuits S/H are connected to a common timing line 78. An address line 104 is connected to the multiplexers 76, 106, 108, 110. The analogue to digital converter 82 is connected to a data line 102 and a timing lines 100.

The parallel outputs of the detectors (apart from the LED stabilisation means) are fed to a multiplexing element 76 that is conventionally implemented as a cascade of analogue multiplexers. Equally the multiplexing is sometimes achieved digitally using control of output enables of bus connected drivers.

The single channel of output is further gain and offset adjusted by an amplifier 80 and then input to an Analogue to Digital Converter (ADC) 82. The ADC will, on command, convert the signal value to a digital representation at a specified level of precision. This value is then read by a computational device (not shown), typically a microprocessor and read into a memory location.

The computational element operates on the scattering data to fit it to known Fraunhofer and/or Mie Scattering theories to evaluate the particle size distribution by evaluating the best fit distribution that would produce the detected scattering.

In prediction of the back scatter signal expected from theory it has been found necessary to take account of the reflection properties of the cell windows 18, 20 and those of any other plane surface in the scattering region, such a protection windows, etc.

The back-scatter signals are relatively weak at all particle sizes and only become significant when the particle sizes become small and scattering becomes more isotropic. Thus as size reduces the strongly dominant forward scattering becomes weaker until it has reached the same intensity as the back-scatter.

Figure 9:
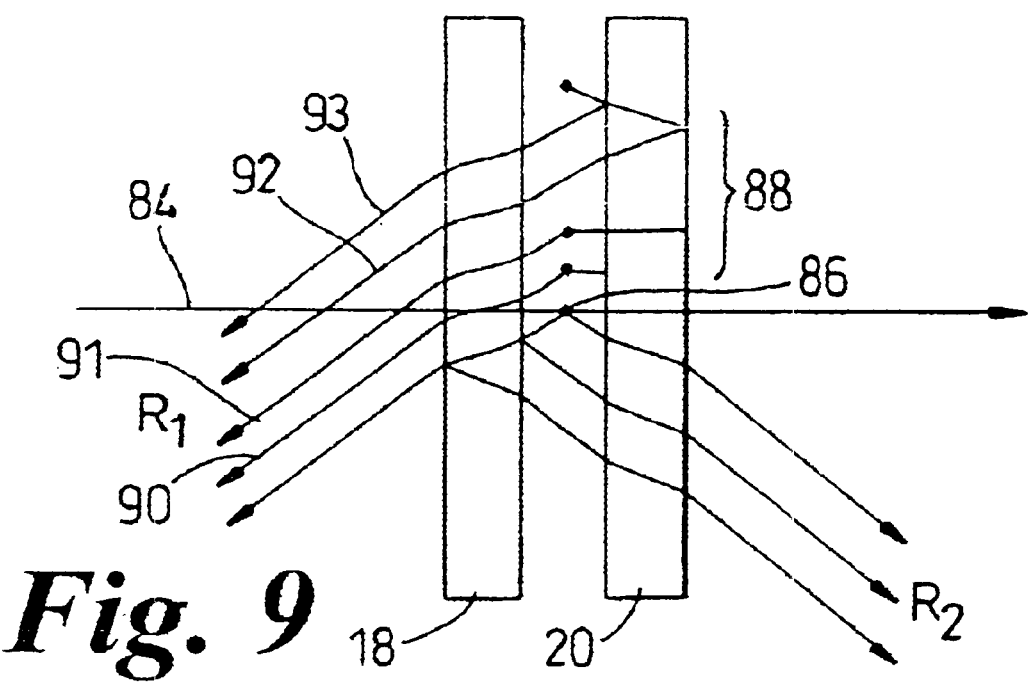
FIG. 9 shows the reflections occurring from a sample cell of the system.

This situation means that if forward scatter light were to be back reflected, even inefficiently (for example from a cell window), then it would significantly corrupt the back-scatter signals. The mechanisms for cell reflection in the standard form of cell are as shown below in FIG. 9.

The principle illumination, or incident beam, is shown above at 84 on the main axis, propagating left to right. The main scattering components are shown from a notional single particle 86. These rays are those predicted by the use of conventional light scattering theories, such a Fraunhofer or Mie, etc.

Additional ray paths 88 exist if each plane surface of the cell 16 is considered to have finite reflectivity. These are shown above the incident beam 84 and displaced higher on the figure to aid visibility. Starting from the centre and working upwards we have, the 0° reflection of the unscattered beam 90, 91 that is back-reflected and then forward scattering off the particle. The forward scattering produces two beams since there are two cell window surfaces. Then there are the two components 92, 93 caused by reflection of the forward-scattering light emerging from the cell without further scattering.

Any other plane surfaces in the system demonstrate the same basic behaviour, and therefore any further surfaces between cell and detector generate similar signals. Because the detectors have limited collection range caused by the typical apertures present in the optical system it is generally only 0° back reflections that needs to be accounted for with these additional windows. The 0° reflected beam propagates back through the system until it again passes through the cell and any subsequent scattering is then directly in the line of sight of the detectors.

Each reflection depends upon the reflectivity of the surface involved and the angle of incidence of the beam. By the appropriate use of anti-reflection coatings it is possible to minimise reflections, particularly those effects involving 0° reflections. However for high angle of incidence reflectively values of up to 10% can be experienced, even with optimised surfaces/coatings.

The original back-scattered light can also be forward scattered, although this is usually a small effect due to the strong dominance of the forward signal. However for the smallest sizes, where light has become almost completely isotropic it is useful to take account of the reflection of the back scattered components. In the diagram above this is shown at $R_2$ displaced downwards from the diagram centre.

Reflections are cumulative since the first reflected beam might suffer further reflection before the exiting the cell. However whilst reflectivities are <10% any second reflection will have reduced to a <1% effect and thus can be safely ignored. For the purposes of the models it is normally sufficient to include only first reflection behaviour for each mechanism.

The overall effect of these multi-component reflections is simple, a practical reflectivity $R_1$ and $R_2$ can be determined for the cell which describe the grossed up cell behaviour at the scattering angle concerned. Thus $R_1$ describes the effect where light originally scattered to angle θ will be reflected into the back-scatter angle 180−θ. Generally because of their different composition $R_1$ and $R_2$ are not identical, despite the apparent symmetry of the cell.

This makes clear that the back-scatter angle 180−θ is corrupted by a signal component from forward angle θ. To take account of this theoretically it is necessary to integrate the appropriate light scattering theory over the back-scatter angles, and those forward angles mirrored by the cell. These two signals can then be combined according to the reflectivity $R_1$. The need to account for the mirror angles doubles the computational load for the calculation of the scattering matrices, essential to the analysis of data to particle size.

An advantage accrues in this computation if the large angle detectors 34, 36 and back scatter detectors 38, 40 operate at angles that are mirror symmetric and are preferably identical in construction. If for example back scatter detector 40 is mirror symmetric with large angle detector 36 then the integration of reflection angles appropriate to back scatter detector 40 has already been accomplished in computing the forward scatter at large angle detector 36. Thus the necessary reflection corrections can be performed using the standard theory. For the case mentioned the correction would be $$BS_2{}^* = (1-R_2)(BS_2 + R_1 \cdot FS_1)$$

$BS_2$=reading at back scatter detector 40
$FS_1$=reading at large angle detector 36

Where $BS_2{}^*$ is the corrected scattering matrix signal under any given condition where $BS_2$ and $FS_1$ were the original theoretical predictions without reflections assumed.

Thus we compensate the detected back scatter signals by an amount dependent upon the detected forward scatter signals to take into account reflections.

The effect of accounting for cell reflections in the performance of the size analysis is extremely beneficial at all particle sizes. Without cell reflection correction the system under-predicts the amount of back-scatter light present for a given material. The excess causes the instrument to assume that sub micron particles are present too, since they can give rise to back-scatter signals whilst barely altering the forward scatter data.

By accounting for the cell reflections the system is able to correctly predict the back-scatter signal excess, thus improving accuracy of measurement for sub micron sizes.

The mirror symmetry of the large angle detectors 34, 36 and the back scatter detectors 38, 40 detectors offers a computational advantage in the calculation of scattering matrices only, it does not affect the sizing performance directly.

Although compensation for reflections from cell surfaces have their major use in back scattering we may additionally or alternatively compensate the detected signals for forward scattering using input from detected back scatter signals, but this is likely to be far less significant.

Previously it has not been thought worthwhile to compensate for reflections. However, it has been discovered that the reflections create larger errors than originally thought. Indeed at some particle sizes the error due to reflected light is significant. At these particle sizes a minimum amount of light is back scattered toward the emitter whilst a maximum amount of light is reflected and we have found that particular particle sizes are 0.3 μm (when illuminated with red light) and 0.2 μm (when illuminated with blue light).

Although the windows 18, 20 of the system are coated with anti-reflective coatings it is difficult of optimise the coatings for both the wavelengths of light in the system. The coating may be optimised for one particular wavelength and consequently be less than optimised for the other wavelength. It may therefor be especially advantageous to account for reflections of light in an apparatus utilising more than wavelength of light.

In the absence of particles in the cell 16 there is no scattering of the laser 2 beam or beam from the LED 42 and thus in theory the entire beam will pass through the hole 48 in the wafer 46 and onto the transmission detector 50. If particles are introduced to the cell 16 of the system then light is both absorbed by the particles and scattered into other angles resulting in a reduction in the signal received on the transmission detector 50. It is normal to measure the transmission before the introduction of particles $T_{RS}$ and when particles are present in the cell 16, $T_{RS}$. This is used to calculate the "obscuration" of the laser beam, which is given by:

$$O_R = 1 - T_{RS}/T_{RS}$$

The obscuration of the laser beam $O_R$ is used both in the data processing to obtain particle size and as a diagnostic to assist in setting up a suitable particle concentration range for a particular measurement.

The scattered light from particles present in the cell 16 spreads out into all angles, having a size dependant angular intensity distribution $S(d,\theta,\phi)$. The d represents the particle size, $\theta$ the scattering angle and $\phi$ the azimuth angle. Because particles are normally in random orientation within the cell, and many thousands of particles are scattering simultaneously, the azimuthal dependence of scattering is lost. It is normal practise to sacrifice any potential size information in the $\phi$ variation to avoid the problems that would arise in needing to align particles practically within the cell. Thus these systems typically concern themselves with measurement of the $\theta$ variation, assuming $\phi$ symmetry, reducing scattering dependence to $S(d, \theta)$ Broadly, very small particles scatter light isotropically whereas large particles scatter into a very small angle around the unscattered beam. There are a number of theories available that allow complete prediction of this $\theta$ variation for a known sized particle and thus by measuring it the size of the scattering particles can be inferred.

The LED transmission detector 45 is used in an identical manner to the transmission detector 50 for the laser beam, which is to find the sample obscuration of the blue light.

$$O_R = 1 - T_{RS}/T_{RS}$$

Using the same terminology as described earlier for the red obscuration.

Because the blue beam path is offset in the plane perpendicular to the detector plane by a relatively small amount the effect of the offset is negligible in altering the scattering angles subtended by the large angle 38, 40 and back scatter 34, 36 detectors. As a consequence these detectors can be considered as occupying identical angles of detection in measurement of the blue beam (beam from LED 42) when compared to measurement of the red beam (beam from the laser 2). Alternatively, some compensation may be applied but we do not believe it to be necessary. The detectors 34, 36, 38, 40 have gain characteristics that are different at the wavelengths emitted by the laser 2 and the LED 42. In addition the data from each detector 34, 36, 38, 40 is weighted differently in the analysis for the data obtained for the light emitted from the laser 2 and the LED 42. For these reasons the large angle 34, 36 and back scatter 38, 40 detectors have two gain calibrations recorded, one for light emitted from the laser 2 and the other for light emitted from the LED 42.

The measurement of the transmission of the light emitted from the laser 2 (and light emitted from the LED 42 in our system) is generally used in prior art systems to ensure that the particle concentration in the cell 16 is in an optimum range. The particle concentration must lie within a specified range if the signal processing is to be effective. At high concentrations it is important that multiple scattering does not occur, and if too low there is insufficient signal created on the detectors for reliable measurement. These two limits are usually expressed as an obscuration range so that the user can easily determine from the data display that both criteria are satisfactory. For example in one prior art system it is required to ensure that the obscuration signal lies in the following range:

$$0.01 < O_R < 0.5$$

In the preferred embodiment a further use has been made of these signals. Each attenuation is converted to a synthetic data point, the "Extinction". The extinction is related to transmission by the following formula $$E_R = -A.ln(T_{RS}/T_{RS})$$

Where $E_R$ is the extinction of the blue beam and A is an arbitrary constant.

The important property of the extinction data that is useful is that it behaves linearly with concentration whereas the original transmission and obscuration behave non-linearly. This allows the extinction to be treated as a data point and the scaling constant A can be set to scale the signal so that it fits into the data set with an appropriate significance. Thus two additional data points are derived from the transmission values and added to the data set that is analysed, the Extinction points for light emitted from the laser 42 and emitted from the LED 42.

These data points are useful in that they are sensitive to the detection of small particles. Such materials generate weak scattering signals but are effective at reducing the beam transmission, effectively generating high extinction. The combination therefore of high extinction and low scattering is indicative of fine materials. The disparity between the extinction of light emitted from the laser 2 and the LED 42 values also contains useful small size information. For larger sizes the extinction values are identical, for fine particle sizes the extinction differs. The difference increases as size reduces within a useful size range. The extinction data points therefore provide size discrimination information for small particles. They are approximately equivalent in information terms to the back-scatter detectors 38, 40.

In the preferred embodiment there are back scatter 38, 40 detectors provided and it is valid to question why the extinction points are also included, if they provide the same size information. There is a further benefit to sub-micron capability given by these points however, when the sample concentration is low the back-scatter data becomes small, poorly resolved and hence subject to substantial experimental error. The absence of extinction points would affect the ability of the preferred embodiment to repeatably measure small sizes. The transmission measurements are much easier to make and remain precise after the back-scatter signals have become unreliable.

Thus the extinction data points enhance the performance extending the size range over that obtained using the back scatter 38, 40 signals alone.

The transmission measurements of the light emitted from the laser 2 and LED 42 are made one after the other and not simultaneously. During background or sample measurements the sequence is the same. The shutter in front of the laser is turned on (passing the light from the laser 2), the blue LED 42 is switched off and measurement using light from the laser 2 is performed. When the measurement is completed (for example immediately afterwards) the shutter is introduced to block light from the laser 2 and the LED 42 is switched on. The same measurement process can then take the data obtained from the light emitted from the LED 42.

The measurement points using light emitted from the LED 42 are extracted from this second measurement and inserted into the measurement data obtained from measurements taken from light emitted from the laser 2, extending it. As the data sets are combined the respective gains of both systems are adjusted to comply with a previous system calibration. The combined data set becomes the resultant experimental data that is analysed to obtain particle size using the computational element 77 and computational device.

As particles pass through the cell 16 many thousands of particles are simultaneously illuminated and the signal received on a detector is a continuous optical summation of the scattering from all particles within the cell 16. As the particles pass through the cell 16 the sample volume population fluctuates statistically and thus the signal develops a noise like fluctuation reflecting the local population variation.

It is normal for a detector signal to be integrated over a significant time period in order to ensure that the angular intensity curve analysed is representative of a large number of particles. The integration process thus removes the statistical noise and ensures that the average is representative of the entire population of the material. This integration can be performed conventionally either by the analogue electronics, by digital electronics, by summation in a microprocessor or stand-alone computer such as a PC. In the preferred embodiment it is normally performed by a microprocessor built into the system.

In any event the detector data is produced simultaneously from all angles during any measurement from either one of the light sources 2, 42.

The parallel data produced by the system is fed to the circuitry of FIG. 8 which produces a serial stream that can be read through a common interface.

The Sample and Hold function is operated by a control signal on the common timing line 78 and effectively freezes the signal at a single time instant. By ensuring that data from all detectors is frozen at the same time before conversion it is ensured that no concentration fluctuations of the sample in the cell 16 become converted into apparent angular fluctuations by the serialisation process that follows.

At the time at which measurement is required the control signal goes from tracking to hold mode which locks the signal readings on the outputs of the sample and hold circuits. It is important that data is then converted quickly so that signal droop does not occur.

The computational device connected to the output of the ADC runs an algorithm that accesses each detector channel in sequence until all valid channels for that wavelength has been collected, digitised and held in memory. The complete data set from this single sample and hold event is called either a "sweep" or a "snap" and is the smallest unit of measurement of data.

These snaps of complete system data are then taken successively and summed by the computational element 77 to form an experiment. A snap requires a defined minimum time interval to complete, and multiple snaps are performed at the fastest rate that the computational device can accommodate. Thus the measurement time is determined by the number of snaps requested, usually controllable by the user.

Because of the time sequential nature of the measurements using light emitted by the laser 2 and the LED 42 the measurement is in fact accumulated in two sub-experiments. When the beam from the laser is incident upon the cell 16 the requested number of snaps of integration are first summed, the first experiment. Then the instrument switches automatically so that light emitted from the LED 42 is incident upon the cell 16 and performs the same number of snaps again, accumulating a new record, the second experiment. For the experiment using the LED 42 to emit the light most of the data accumulated is unused in our preferred embodiment since only the large angle 34, 36 and the back scatter 38, 40 signals are valid. These data points are extracted by the computational element 77 from the second experiment and interleaved with the first experiment extending it (extending the angular range of scattering over which reliable meaningful signals have been collected). At this point any scale compensation required between the optical components for light emitted from the laser 2 and the LED 42 is applied. Thus the computational device uses experimental results accumulated from the use of light emitted from both the laser 2 and the LED 42.

The obscuration signals for light emitted from both the laser 2 and the LED 42 from the transmission detector 50 and the LED transmission 45 detectors are also read by being passed through the multiplexer and ADC to the computational device. Similarly the signal from the laser power monitor 10 is fed through to allow the signals using the light emitted from the laser 2 to be scaled to be adjusted for any laser power variation. An obvious extension of this approach would be, as mentioned earlier, the reading of the blue monitor signal for the same purpose on blue data.

The apparatus may be provided with a visible light means situated at a top most region of the apparatus acting as a power on/off display. That is the light means may be adapted to emit light when the apparatus is in a powered on situation, and off when there is no power to the apparatus. The light means may be situated such that it is visible from substantially any angle around the machine which is advantageous in that it allows a user to readily determine whether or not there is power to the apparatus.

The light level measurements taken using light from each detector may be manipulated so that the measurements comprise a single data set as if the measurements had been taken by a single wavelength of light.

What is claimed is:

1. A particle size distribution analysis apparatus comprising a sample measurement zone defining a sample of particles, a light emitting means for providing a source of light incident upon the sample measurement zone, and at least a first detection means for measuring light levels in the apparatus at particular scattering angles and output a signal to a computation means for calculating said particle size distribution enabling the particle size distribution of particles contained within said sample to be determined, wherein said computation means is arranged to substantially completely compensate for the reflection, by at least one window of said measurement zone, of light that has previously been scattered by said particles, at each of said scattering angles when calculating said particle size distribution.

2. An apparatus according to claim 1 wherein there is provided a second detection means and said computation means uses measurements taken from said first detection means and measurements taken from said second detection means in order to take in to account reflections.

3. An apparatus according to claim 2 wherein an angle at which the second detection means is inclined relative to an optical axis of said light emitting means is equal to 180° minus an angle at which said first detection means is inclined relative to the optical axis.

4. An apparatus according to claim 2 wherein said computation means predicts, in use, measurements taken from said second detection means based upon measurements taken from said first detection means to take in to account reflections.

5. An apparatus according to claim 2 wherein said second detection means comprises a back scatter detector which is situated substantially at an obtuse angle from the axis of a beam of light emitted from said light emitting means taking the direction of travel of the light as 0°.

6. An apparatus according to claim 5 wherein said obtuse angle is substantially in the range 90° to 180°.

7. An apparatus according to claim 5 wherein said obtuse angle is substantially in the range 110° to 170°.

8. An apparatus according to claim 5 wherein there are provided a plurality of said back scatter detectors.

9. An apparatus according to claim 2 wherein there are a plurality of first detection means and the same number of second detection means wherein said first and said second detection means are inclined symmetrically relative to said measurement zone.

10. An apparatus according claim 2 wherein said first and said second detectors are of substantially the same construction.

11. An apparatus according to claim 1 wherein said first detection means comprises a large angle detector which is situated substantially in the range 90° to 0° from the axis of a beam of light emitted from said light emitting means taking the direction of travel of the light as 0°.

12. An apparatus according to claim 11 wherein said large angle detector is situated substantially in the range of 70° to 40°.

13. An apparatus according to claim 11 wherein there is provided a plurality of said large angle detectors.

14. A method of improving the accuracy of a particle size distribution calculation performed by illuminating a sample with light from a light emitting means and measuring an amount of light scattered by the sample comprising providing at least a first detection means and substantially completely compensating for reflection by at least one window of a measurement zone of light, that has previously been scattered by the particles at at least two scattering angles.

15. A method according to claim 14 which comprises providing a second detection means and predicting measurements taken from said first detection means by using measurements taken from said second detection means.

16. A method according to claim 15 in which a measurement taken from said second detection means is predicted by using measurements taken by said first detection means.

17. A method according to claim 15 which comprises predicting a measurement from one of the first or second detection means detecting light scattered having a directional component towards said light emitting means by using a measurement from the other of the first or second detection means detecting scattered light having no directional component toward said light emitting means.

18. A method according to claim 15 which comprises predicting a measurement from one of the first or second detection means detecting light having no directional component towards said light emitting means by using a measurement from the other of the first or second detection means detecting scattered light having a directional component toward said light emitting means.

19. A method according to claim 15 which comprises providing said first and second detection means at substantially mirror symmetric angles relative to a beam of light emitted by said light emitting means.

20. A method according to claim 15 which comprises providing a plurality of detectors for said first detection means.

21. A method according to claim 15 which comprises providing a plurality of detectors for said second detection means.

22. A particle size distribution analysis apparatus comprising a cell for containing a sample of particles, a monochromatic light source for illuminating the sample, first and second photodetectors for measuring light scattered by the particles, a processor for processing measurements of the scattered light such that a reflection, by a surface of the cell, of light that has previously been scattered by said particles are taken into account when calculating the particle size distribution, wherein said processor substantially completely compensates for the reflection of light that has previously been scattered by said particles, when calculating said particle size distribution.

* * * * *